United States Patent [19]

Donner

[11] 4,326,806
[45] Apr. 27, 1982

[54] COPPER LIQUOR ANALYZER

[75] Inventor: Gary L. Donner, Palos Verdes Peninsula, Calif.

[73] Assignee: Texaco Inc., White Plains, N.Y.

[21] Appl. No.: 105,455

[22] Filed: Dec. 20, 1979

[51] Int. Cl.³ .................. G01N 21/85; G01N 21/09
[52] U.S. Cl. .................. 356/410; 250/576; 356/246; 356/414; 356/440
[58] Field of Search ........... 356/410, 411, 414, 436, 356/440, 246; 250/576

[56] References Cited

U.S. PATENT DOCUMENTS

| | | | |
|---|---|---|---|
| 3,076,375 | 2/1963 | Donnell | 356/410 |
| 3,524,709 | 8/1970 | Hydina | 356/246 |
| 3,552,864 | 1/1971 | Shields | 356/246 |
| 3,941,487 | 3/1976 | Ehret et al. | 356/411 |
| 4,003,661 | 1/1977 | Yamano | 356/436 |
| 4,152,073 | 5/1979 | Zimmerman | 356/410 X |

*Primary Examiner*—Vincent P. McGraw
*Attorney, Agent, or Firm*—Carl G. Ries; Robert A. Kulason; Ronald G. Gillespie

[57] ABSTRACT

A copper liquor analyzer includes a sample cell through which a portion of a copper liquor stream passes. Light of a predetermined wavelength is passed through the copper liquor in the sample cell. A detector circuit receives the passed light from the sample cell and provides an output corresponding to the strength of the copper liquor in accordance with the received light.

7 Claims, 6 Drawing Figures

COPPER LIQUOR ANALYZER

BACKGROUND OF THE INVENTION

Field of the Invention

The present invention relates to analyzers in general and, more particularly, to an on-stream analyzer for a liquid solution.

SUMMARY OF THE INVENTION

A copper liquor analyzer includes a sample cell through which a portion of a stream of copper liquor flows. Light of a predetermined wavelength is passed through the copper liquor in the sample cell. A detector receives the passed light and provides an output corresponding to the strength of the copper liquor in accordance with the received light.

The objects and advantages of the invention will appear more fully hereinafter from a consideration of a detailed description which follows, taken together with the accompanying drawings wherein one embodiment of the invention is illustrated by way of example. It is to be expressly understood, however, that the drawings are for illustration purposes only and are not to be construed as defining the limits of the invention.

DESCRIPTION OF THE INVENTION

Figure 1:
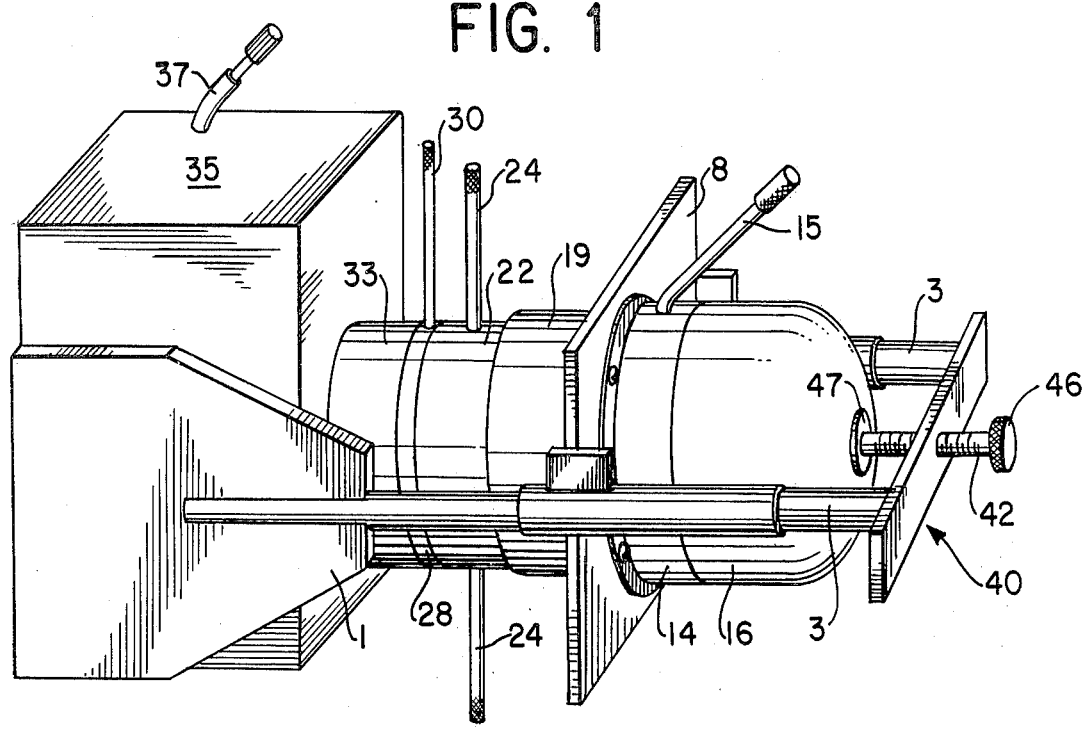
FIG. 1 is an assembly drawing of a copper liquor analyzer constructed in accordance with the present invention.
Figure 5:
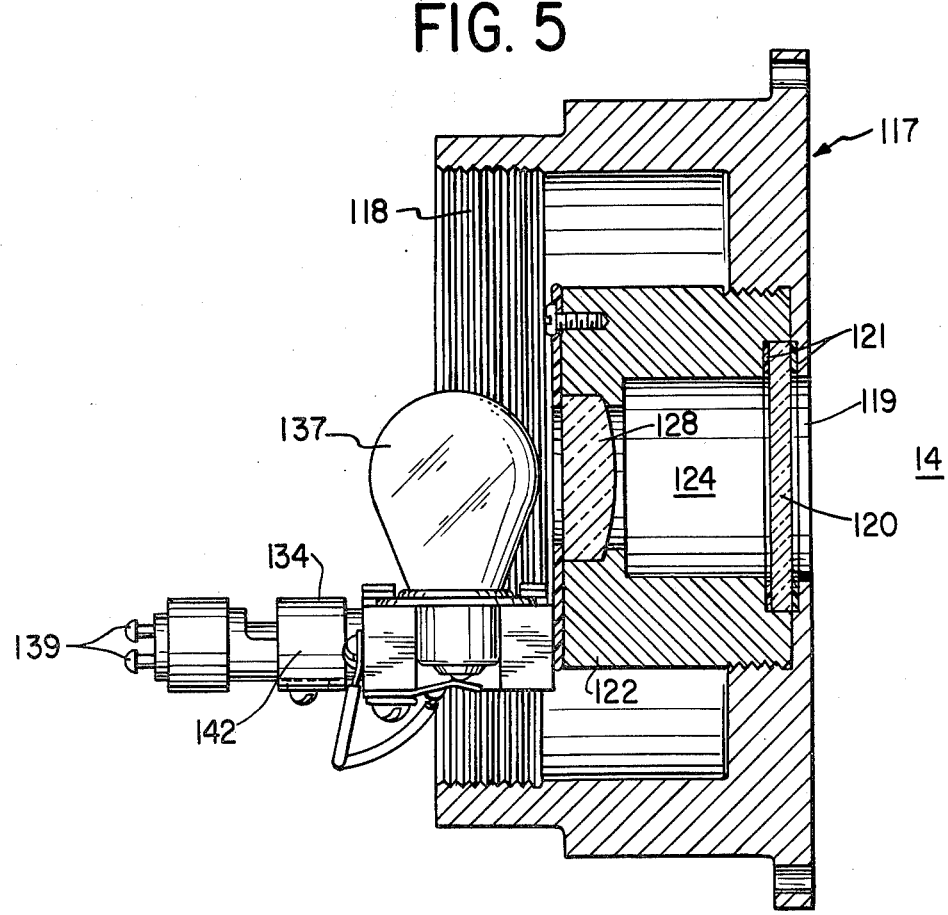
FIGS. 4 and 5 are assembly drawings of the detector unit and the light unit, respectively, shown in FIG. 1.

Referring now to FIG. 1, a copper liquor analyzer includes supports 1 having affixed thereto by conventional means runners 3 spaced a predetermined distance apart. A mounting bracket 8 is mounted so that it is capable of moving along the runners 3. Mounted on said mounted bracket 8 during normal operation is a light unit 14 having an electrical cable 15 for providing power to the light unit 14.

A shell 16 is threaded into light unit 14 to form a single assembly. Affixed to the other side of the mounting bracket 8 is a spacer 19. Adjacent to spacer 19 is a sample cell 22 having entrance and exit tubing 24 which may be attached to a line through which the copper liquor flows to be analyzed. An air purge cell 28, with a tubing 30 suitable for connection to an air supply, separates a light detector unit 33 from sample cell 22. Unit 33 is mounted on an electronic package 35 which has an electrical cable 37 that connects with cable 15 by a cable and connectors not shown. A support bracket 40 affixed to runners 3 has a threaded rod 42 passing through it with a knob 46 at one end and a disc 47 at the other end which enables an operator to compress the units 8, 14, 15, 16, 19, 22, 28 and 33 together so that there is proper sealing as hereinafter explained.

Figure 2:
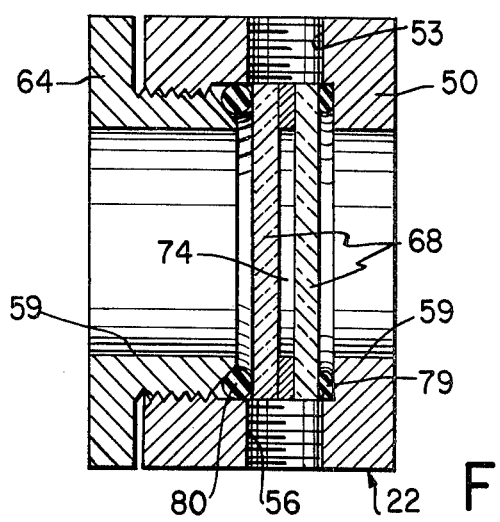
FIG. 2 is an assembly drawing of the sample cell shown in FIG. 1.

Referring now to FIG. 2, sample cell 22 is composed of a body 50 having entrance and exit ports 53 and 56, respectively, threaded for the acceptance of pipes 24, a passageway 59 for the light to pass through and a thread opening. An end ring 64, is threaded into the last mentioned opening and is used to retain glasses 68 separated by a spacer 74 and sealing O-rings 79 and 80.

Figure 3:
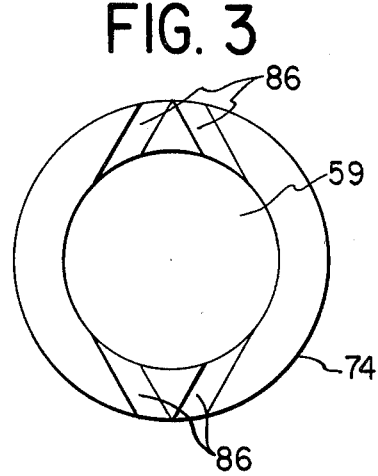
FIG. 3 is a drawing of the spacer shown in FIG. 2.

The surface of spacer 74 is shown in greater detail in FIG. 3, which shows a passageway 59 in spacer 74 for the passage of light. Spacer 74 also has grooved surface 86. The purpose of grooves 86 is to pass the copper liquor in such a manner as to create a swirling action of the copper liquor to provide a cleansing action on glass 68. Glass 68 clarity during operation is further enhanced by the utilization of Corning glass, their part no. 3850. The pores in that glass are small enough so that the copper cannot fill in the glass and thereby reduce the clarity of the glass.

Figure 4:
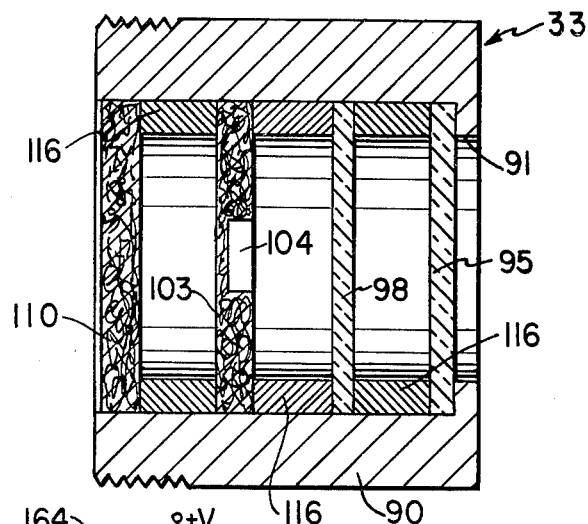

Referring now to FIG. 4, detector 33 comprises a body 90 having threads at one end for mounting into box 35 and a passageway 91 which expands in size for the insertions of other elements. These elements include a glass 95 which may be of the same type of glass 68. A filter 98 of the type manufactured by their part no. 5973, which passes essentially green light. A photo-conductive cell mounting board 103 having an excavation for the mounting of a photo-conductive cell 104 (not shown), a back-up board 110. Boards 103 and 110 are plastic boards. Separating elements 95, 98, 103 and 110 are brass ring spaces 116. It should be noted that the opening in box 35 is less than the largest opening of body 90 so that when detector 33 is mounted in box 35, box 35 keeps elements 95 through 116 in place. Light passing through the sample cell 22 passes through glass 95 and is filtered by filter 98 to impinge upon a photo conductive cell 104 mounted on board 103. Photo cell 104 may be of the type manufactured by Clairox, as their part No. CLM9M. Elements identified by numeral 116 are spaces for the separation of elements 95, 98, 103 and 110.

Light unit 14 has a body 117 having a threaded end 118, for mating with shell 16, and a passageway 119 at the opposite end. A glass 120 is separated from body 117 by spacer 121. Another body 122 is screwed into body 117 and has an opening to accept glass 120. However, glass 120 is separated from body 122 by spacer 121 so that when body 122 is threaded into body 117, it holds glass 120 in place. Body 122 has a passageway 124 which narrows down and again expands so that a collimating lens 128 is placed in the expanded portion of passageway 124. A lamp assembly includes a lamp fixture 134 in which there is mounted a lamp 137. Also mounted in fixture 134, although it cannot be seen, is a photo diode whose terminals 139 are shown. Lamp assembly 134 has an opening so that light from the lamp falls on the photo diode. There is a movable shield 142 which controls the size of the opening and hence the quantity of light impinging on the photo diode. The light from lamp 137 is collimated by lens 128 and passes through glass 119. The current provided to lamp 137 controls the brilliance of lamp 137, said current is controlled by photo diode in fixture 134 which is part of a control system in a power supply regulating the current.

Figure 6:
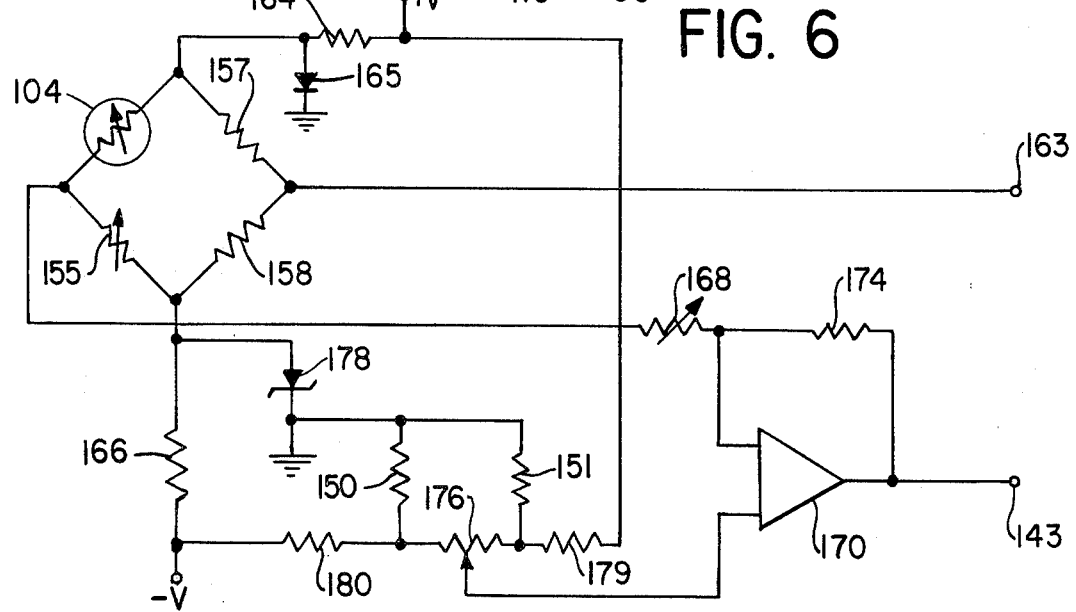
FIG. 6 is a schematic diagram of the detector unit shown in FIG. 1.

With reference to FIG. 6, photo diode 104 forms part of a bridge circuit with a variable resistor 155 and resistors 157, 158. The common node between photo diode 104 and resistor 157 is connected to a biasing resistor 164, receiving a +V biasing voltage, and to a zener diode 165. Zener diode 165 is also connected to ground. The common connection between resistors 155 and 158 is connected to another biasing resistor 166, receiving a negative DC voltage −V. The common connection between photo diode 104 and resistor 155 is connected to a variable gain control resistor 168 which in turn is connected to one input of an amplifier 170 and to a feedback resistor 174. Feedback resistor 174 is connected to a common connection of the output of amplifier 170 and terminal 143. The common node between resistors 157 and 158 is connected to a terminal 163.

A zener diode 178 connects the common connection between resistors 155 and 158 with ground.

The positive biasing voltage $+V$ is also supplied to a balancing resistor network with zero adjustment which includes resistor 179, potentiometer 176 and resistor 180 connected in series and receiving the negative and positive biasing voltages at opposite ends. Resistors 150 and 151 connect the common connections between resistors 176, 180 and resistors 176 and 179, respectively, to ground. The wiper arm of potentiometer 176 is connected to another input of amplifier 170 and, as noted before, is used to make zero adjustments. The output signal, corresponding to the strength of the copper liquor solution, appears across terminals 143 and 163.

What is claimed is:

1. A copper liquor analyzer comprising sample cell means for having a portion of a stream of copper liquor flowing through it, means for passing light of a predetermined wavelength through the copper liquor in the sample cell means, and output means receiving the light passed through the copper liquor for providing an output corresponding to the strength of the copper liquor in accordance with the received light; and said sample cell means includes entrance means for receiving the copper liquor and exit means for passing the copper liquor, light rays passage means for the passage of the light, arranged so that the entrance and exit means are connected to it, a pair of glasses, each glass having pores not greater than a predetermined size to prevent filling of the pores by copper and being spacially arranged with the passageway means, the entrance means and the exit means, and first spacer means for separating the glasses in a manner so that the copper liquor flows between the glasses and so that the light passes through the flowing copper liquor.

2. An analyzer as described in claim 1 in which the light is provided at a constant brilliance.

3. An analyzer as described in claim 2 in which the first spacer means has a hollow center and has one surface with grooves in a manner so that the copper liquor flows through the grooves to create a convaluted swirling action within the hollow center between the glasses before exiting and so that the hollow center provides a passageway for the light.

4. An analyzer as described in claim 3 in which the light means includes lamp means for providing light a collimating lens for collimating some of the light emitting by the lamp means, filter means for filtering the collinated light to provide the light of the predetermined wavelength, photo detector means for providing an output corresponding to the brilliance of the light in the lamp, and means for controlling the light from the lamp in accordance with the output from the photo detector means so as to maintain a constant brilliance.

5. An analyzer as described in claim 4 in which the detector means includes a resistance bridge circuit means for providing output corresponding to a voltage across the bridge, said resistance bridge circuit means including a photo cell means for varying its resistance in accordance with light detected by the detector means so as to vary the voltage across the bridge, means connected to the resistance bridge for amplifying said voltage to provide the output corresponding to the strength of the copper liquor.

6. An analyzer as described in claim 1 in which the light means is enclosed in a first housing, the sample cell means is enclosed in a second housing and the output means is enclosed in a third housing, and further comprising means for clamping the three housings together in a manner so that the second housing separates the first and third housings and so that the light from the light means passes through the cell means to the output means.

7. An analyzer as described in claim 6 in which the clamping means has a pair of brackets attached to the third housing means; a pair of runners, each runner being affixed to a corresponding bracket; a fixed plate attached to the ends of the runners away from the brackets and having a threaded center hole; a movable mounting plate adapted to have the first housing means mounted thereon and affixed to the runners so that the mounting plate is free to move along the runners and having a passageway for light; and a rod threaded through the fixed plate adapted at one end to bear against the first housing and adapted at the other end to be operated in a manner so as to have the rod bear against the first housing so as to clamp first and second housings against the third housing or so as not to bear against the first housing so that the first or second housing may be removed.

* * * * *